(12) United States Patent
Hawkins et al.

(10) Patent No.: US 9,421,025 B2
(45) Date of Patent: *Aug. 23, 2016

(54) SHOCKWAVE VALVULOPLASTY CATHETER SYSTEM

(71) Applicant: SHOCKWAVE MEDICAL, INC., Fremont, CA (US)

(72) Inventors: Daniel Hawkins, Fremont, CA (US); John M. Adams, Snohomish, WA (US)

(73) Assignee: Shockwave Medical, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,155

(22) Filed: Apr. 22, 2015

(65) Prior Publication Data

US 2015/0238209 A1    Aug. 27, 2015

Related U.S. Application Data

(63) Continuation of application No. 12/611,997, filed on Nov. 4, 2009, now Pat. No. 9,044,618.

(60) Provisional application No. 61/111,600, filed on Nov. 5, 2008.

(51) Int. Cl.
```
A61B 17/22    (2006.01)
A61M 25/10    (2013.01)
A61N 1/38     (2006.01)
A61N 1/05     (2006.01)
```

(52) U.S. Cl.
CPC ...... *A61B 17/22022* (2013.01); *A61M 25/1002* (2013.01); *A61N 1/38* (2013.01); *A61B 2017/22025* (2013.01); *A61B 2017/22062* (2013.01); *A61B 2017/22098* (2013.01); *A61M 2025/1072* (2013.01); *A61N 1/056* (2013.01)

(58) Field of Classification Search
CPC ................... A61B 17/22004; A61B 17/22012; A61B 17/2202; A61B 17/22022; A61B 17/2203; A61B 2017/2207; A61B 2017/22021; A61M 25/1002; A61M 2025/1045; A61M 2025/1072; A61N 1/056; A61N 1/38

See application file for complete search history.

(56) References Cited

U.S. PATENT DOCUMENTS 3,413,976 A    12/1968  Roze
3,785,382 A    1/1974   Schmidt-Kloiber et al.
(Continued)

FOREIGN PATENT DOCUMENTS

AU    2009313507 B2    11/2014
CN    101043914 A      9/2007
(Continued)

OTHER PUBLICATIONS

Office Action received for Canadian Patent Application No. 2,727,429, mailed on Apr. 14, 2015, 4 pages.
(Continued)

*Primary Examiner* — Sarah W Aleman
(74) *Attorney, Agent, or Firm* — Morrison & Foerster LLP

(57) ABSTRACT

A valvuloplasty system comprises a balloon adapted to be placed adjacent leaflets of a valve. The balloon is inflatable with a liquid. The system further includes a shock wave generator within the balloon that produces shock waves. The shock waves propagate through the liquid and impinge upon the valve to decalcify and open the valve.

16 Claims, 2 Drawing Sheets

(56) References Cited

U.S. PATENT DOCUMENTS

| | | | |
|---|---|---|---|
| 3,902,499 | A | 9/1975 | Shene |
| 4,027,674 | A | 6/1977 | Tessler et al. |
| 4,030,505 | A | 6/1977 | Tessler |
| 4,662,126 | A | 5/1987 | Malcolm |
| 4,671,254 | A | 6/1987 | Fair |
| 4,685,458 | A | 8/1987 | Leckrone |
| 4,809,682 | A | 3/1989 | Forssmann et al. |
| 4,878,495 | A * | 11/1989 | Grayzel ............... A61M 29/02 604/101.01 |
| 4,900,303 | A | 2/1990 | Lemelson |
| 5,009,232 | A | 4/1991 | Hassler et al. |
| 5,046,503 | A | 9/1991 | Schneiderman |
| 5,057,103 | A | 10/1991 | Davis |
| 5,057,106 | A | 10/1991 | Kasevich et al. |
| 5,061,240 | A * | 10/1991 | Cherian ............ A61B 17/22032 604/908 |
| 5,078,717 | A | 1/1992 | Parins et al. |
| 5,102,402 | A | 4/1992 | Dror et al. |
| 5,103,804 | A | 4/1992 | Abele et al. |
| 5,152,767 | A | 10/1992 | Sypal et al. |
| 5,152,768 | A | 10/1992 | Bhatta |
| 5,154,722 | A | 10/1992 | Filip et al. |
| 5,176,675 | A | 1/1993 | Watson et al. |
| 5,195,508 | A | 3/1993 | Muller et al. |
| 5,245,988 | A | 9/1993 | Einars et al. |
| 5,246,447 | A | 9/1993 | Rosen et al. |
| 5,281,231 | A | 1/1994 | Rosen et al. |
| 5,295,958 | A * | 3/1994 | Shturman ........ A61B 17/22012 604/103.07 |
| 5,324,255 | A | 6/1994 | Passafaro et al. |
| 5,336,234 | A | 8/1994 | Vigil et al. |
| 5,368,591 | A | 11/1994 | Lennox et al. |
| 5,395,335 | A | 3/1995 | Jang |
| 5,417,208 | A | 5/1995 | Winkler |
| 5,425,735 | A | 6/1995 | Rosen et al. |
| 5,472,406 | A | 12/1995 | De La Torre et al. |
| 5,505,702 | A | 4/1996 | Arney |
| 5,582,578 | A | 12/1996 | Zhong et al. |
| 5,603,731 | A | 2/1997 | Whitney |
| 5,609,606 | A | 3/1997 | O'boyle |
| 5,662,590 | A | 9/1997 | De La Torre et al. |
| 5,846,218 | A | 12/1998 | Brisken et al. |
| 5,893,840 | A | 4/1999 | Hull et al. |
| 5,931,805 | A | 8/1999 | Brisken |
| 6,007,530 | A | 12/1999 | Doernhoefer et al. |
| 6,033,371 | A | 3/2000 | Torre et al. |
| 6,080,119 | A * | 6/2000 | Schwarze ............... G10K 15/06 367/147 |
| 6,083,232 | A | 7/2000 | Cox |
| 6,113,560 | A * | 9/2000 | Simnacher ............ G10K 15/06 367/147 |
| 6,146,358 | A | 11/2000 | Rowe |
| 6,186,963 | B1 | 2/2001 | Schwarze et al. |
| 6,210,408 | B1 | 4/2001 | Chandrasekaran et al. |
| 6,217,531 | B1 | 4/2001 | Reitmajer |
| 6,267,747 | B1 * | 7/2001 | Samson ................. A61M 25/10 604/103.01 |
| 6,277,138 | B1 | 8/2001 | Levinson et al. |
| 6,287,272 | B1 | 9/2001 | Brisken et al. |
| 6,352,535 | B1 | 3/2002 | Lewis et al. |
| 6,367,203 | B1 | 4/2002 | Grahame et al. |
| 6,371,971 | B1 | 4/2002 | Tsugita et al. |
| 6,398,792 | B1 | 6/2002 | O'connor |
| 6,406,486 | B1 | 6/2002 | De La Torre et al. |
| 6,440,061 | B1 | 8/2002 | Wenner et al. |
| 6,514,203 | B2 | 2/2003 | Bukshpan |
| 6,524,251 | B2 | 2/2003 | Rabiner et al. |
| 6,589,253 | B1 | 7/2003 | Cornish et al. |
| 6,607,003 | B1 | 8/2003 | Wilson |
| 6,638,246 | B1 | 10/2003 | Naimark et al. |
| 6,652,547 | B2 | 11/2003 | Rabiner et al. |
| 6,689,089 | B1 | 2/2004 | Tiedtke et al. |
| 6,736,784 | B1 | 5/2004 | Menne et al. |
| 6,740,081 | B2 | 5/2004 | Hilal |
| 6,755,821 | B1 * | 6/2004 | Fry ........................ A61N 7/00 604/20 |
| 6,939,320 | B2 | 9/2005 | Lennox |
| 6,989,009 | B2 | 1/2006 | Lafontaine |
| 7,066,904 | B2 | 6/2006 | Rosenthal et al. |
| 7,241,295 | B2 | 7/2007 | Maguire |
| 7,569,032 | B2 | 8/2009 | Naimark et al. |
| 7,618,432 | B2 | 11/2009 | Pedersen et al. |
| 7,951,111 | B2 * | 5/2011 | Drasler ............ A61M 25/1002 604/100.01 |
| 8,162,859 | B2 | 4/2012 | Schultheiss et al. |
| 8,556,813 | B2 | 10/2013 | Cioanta et al. |
| 8,574,247 | B2 | 11/2013 | Adams et al. |
| 8,709,075 | B2 | 4/2014 | Adams et al. |
| 8,728,091 | B2 | 5/2014 | Hakala et al. |
| 8,747,416 | B2 | 6/2014 | Hakala et al. |
| 8,888,788 | B2 | 11/2014 | Hakala et al. |
| 2001/0044596 | A1 | 11/2001 | Jaafar |
| 2002/0177889 | A1 | 11/2002 | Brisken et al. |
| 2003/0004434 | A1 | 1/2003 | Greco et al. |
| 2003/0163081 | A1 | 8/2003 | Constantz et al. |
| 2003/0176873 | A1 | 9/2003 | Chernenko et al. |
| 2003/0229370 | A1 | 12/2003 | Miller |
| 2004/0044308 | A1 | 3/2004 | Naimark et al. |
| 2004/0082859 | A1 | 4/2004 | Schaer |
| 2004/0097996 | A1 | 5/2004 | Rabiner et al. |
| 2004/0249401 | A1 | 12/2004 | Rabiner et al. |
| 2004/0254570 | A1 | 12/2004 | Hadjicostis et al. |
| 2005/0015953 | A1 | 1/2005 | Keidar |
| 2005/0021013 | A1 | 1/2005 | Visuri et al. |
| 2005/0090846 | A1 | 4/2005 | Pedersen et al. |
| 2005/0171527 | A1 | 8/2005 | Bhola |
| 2005/0245866 | A1 | 11/2005 | Azizi |
| 2005/0251131 | A1 | 11/2005 | Lesh |
| 2006/0004286 | A1 | 1/2006 | Chang et al. |
| 2006/0074484 | A1 | 4/2006 | Huber |
| 2006/0184076 | A1 | 8/2006 | Gill et al. |
| 2006/0190022 | A1 | 8/2006 | Beyar et al. |
| 2007/0088380 | A1 | 4/2007 | Hirszowicz et al. |
| 2007/0129667 | A1 | 6/2007 | Tiedtke et al. |
| 2007/0239082 | A1 | 10/2007 | Schultheisse et al. |
| 2007/0239253 | A1 | 10/2007 | Jagger et al. |
| 2007/0244423 | A1 | 10/2007 | Zumeris et al. |
| 2007/0299481 | A1 | 12/2007 | Syed et al. |
| 2008/0077165 | A1 | 3/2008 | Murphy |
| 2008/0097251 | A1 | 4/2008 | Babaev |
| 2008/0188913 | A1 | 8/2008 | Stone et al. |
| 2009/0030503 | A1 | 1/2009 | Ho |
| 2009/0041833 | A1 | 2/2009 | Bettinger et al. |
| 2009/0247945 | A1 | 10/2009 | Levit et al. |
| 2009/0254114 | A1 | 10/2009 | Hirszowicz et al. |
| 2009/0312768 | A1 | 12/2009 | Hawkins et al. |
| 2010/0016862 | A1 | 1/2010 | Hawkins et al. |
| 2010/0036294 | A1 | 2/2010 | Mantell et al. |
| 2010/0094209 | A1 | 4/2010 | Drasler et al. |
| 2010/0114020 | A1 | 5/2010 | Hawkins et al. |
| 2010/0114065 | A1 | 5/2010 | Hawkins et al. |
| 2010/0121322 | A1 | 5/2010 | Swanson |
| 2010/0179424 | A1 | 7/2010 | Warnking et al. |
| 2010/0305565 | A1 | 12/2010 | Truckai et al. |
| 2010/0324554 | A1 | 12/2010 | Gifford et al. |
| 2011/0034832 | A1 | 2/2011 | Cioanta et al. |
| 2011/0118634 | A1 | 5/2011 | Golan |
| 2011/0166570 | A1 | 7/2011 | Hawkins et al. |
| 2011/0257523 | A1 | 10/2011 | Hastings et al. |
| 2011/0295227 | A1 | 12/2011 | Hawkins et al. |
| 2012/0071889 | A1 | 3/2012 | Mantell et al. |
| 2012/0095461 | A1 | 4/2012 | Herscher et al. |
| 2012/0116289 | A1 | 5/2012 | Hawkins et al. |
| 2012/0143177 | A1 | 6/2012 | Avitall |
| 2012/0203255 | A1 | 8/2012 | Hawkins et al. |
| 2012/0221013 | A1 | 8/2012 | Hawkins et al. |
| 2012/0253358 | A1 | 10/2012 | Golan |
| 2013/0030431 | A1 | 1/2013 | Adams |
| 2013/0030447 | A1 | 1/2013 | Adams |
| 2013/0116714 | A1 | 5/2013 | Adams et al. |
| 2013/0150874 | A1 | 6/2013 | Kassab |
| 2014/0005576 | A1 | 1/2014 | Adams et al. |
| 2014/0039513 | A1 | 2/2014 | Hakala et al. |
| 2014/0039514 | A1 | 2/2014 | Adams et al. |

(56) References Cited

U.S. PATENT DOCUMENTS

| | | |
|---|---|---|
| 2014/0046229 A1 | 2/2014 | Hawkins et al. |
| 2014/0046353 A1 | 2/2014 | Adams |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0163592 A1 | 6/2014 | Hawkins et al. |
| 2014/0214061 A1 | 7/2014 | Adams et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2015/0073430 A1 | 3/2015 | Adams et al. |
| 2015/0238208 A1 | 8/2015 | Adams et al. |

FOREIGN PATENT DOCUMENTS

| | | | |
|---|---|---|---|
| DE | 3038445 A1 | 5/1982 | |
| EP | 0442199 A2 | 8/1991 | |
| EP | 571306 A1 | 11/1993 | |
| EP | 2362798 B1 | 4/2014 | |
| JP | 62-275446 A | 11/1987 | |
| JP | 3-63059 A | 3/1991 | |
| JP | 6-125915 A | 5/1994 | |
| JP | 7-47135 A | 2/1995 | |
| JP | 10-99444 A | 1/1998 | |
| JP | 10-513379 A | 12/1998 | |
| JP | 2002-538932 A | 11/2002 | |
| JP | 10-314177 A | 12/2002 | |
| JP | 2004-081374 A | 3/2004 | |
| JP | 2004-357792 A | 12/2004 | |
| JP | 2005-515825 A | 6/2005 | |
| JP | 2006-516465 A | 7/2006 | |
| JP | 2007-532182 A | 11/2007 | |
| JP | 2008-506447 A | 3/2008 | |
| JP | 2011-528963 A | 12/2011 | |
| JP | 2005-95410 A | 4/2015 | |
| WO | 89/11307 A1 | 11/1989 | |
| WO | 96/24297 A1 | 8/1996 | |
| WO | 2004/069072 A2 | 8/2004 | |
| WO | 2005/099594 A1 | 10/2005 | |
| WO | 2006/006196 A2 | 1/2006 | |
| WO | 2006/127158 A2 | 11/2006 | |
| WO | 2007/088546 A2 | 8/2007 | |
| WO | 2007/149905 A2 | 12/2007 | |
| WO | 2009/121017 A1 | 10/2009 | |
| WO | 2009/152352 A2 | 12/2009 | |
| WO | 2010/014515 A2 | 2/2010 | |
| WO | 2010/014515 A3 | 8/2010 | |
| WO | 2010/054048 A3 | 9/2010 | |
| WO | 2011/069025 A1 | 6/2011 | |
| WO | 2011/143468 A2 | 11/2011 | |
| WO | 2013/059735 A1 | 4/2013 | |
| WO | 2013/070750 A1 | 5/2013 | |
| WO | 2014/025620 A1 | 2/2014 | |

OTHER PUBLICATIONS

Notice of Allowance received for U.S. Appl. No. 13/207,381, mailed on Apr. 14, 2015, 7 pages.
Notice of Allowance received for U.S. Appl. No. 13/465,264, mailed on May 8, 2015, 7 pages.
Notice of Allowance received for U.S. Appl. No. 13/646,570, mailed on Mar. 11, 2015, 7 pages.
Non Final Office Action received for U.S. Appl. No. 14/229,735, mailed on May 7, 2015, 8 pages.
Notice of Allowance received for U.S. Appl. No. 14/271,342, mailed on Mar. 13, 2015, 5 pages.
Adams, John M., Unpublished U.S. Appl. No. 14/660,539, filed Mar. 17, 2015, titled "Shockwave Balloon Catheter System", 17 pages.
Extended European Search Report (includes Supplementary European Search Report and Search Opinion) received for European Patent Application No. 09763640.1, mailed on Oct. 10, 2013, 5 pages.
Extended European Search Report and Search Opinion received for European Patent Application No. 09825393.3, mailed on Feb. 28, 2013, 6 pages.
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Final Office Action received for U. S. Appl. No. 12/482,995, mailed on Jul. 22, 2011, 14 pages.
Final Office Action received for U.S. Appl. No. 12/482,995, mailed on Feb. 20, 2014, 11 pages.
Non Final Office Action received for U. S. Appl. No. 12/482,995, mailed on Aug. 13, 2014, 10 pages.
Non Final Office Action received for U. S. Appl. No. 12/482,995, mailed on Jul. 12, 2013, 11 pages.
Non Final Office Action received for U.S. Appl. No. 12/482,995, mailed on Feb. 11, 2011, 27 pages.
Notice of Allowance received for U.S. Appl. No. 12/482,995, mailed on Dec. 24, 2014, 6 pages.
Final Office Action received for U.S. Appl. No. 12/501,619, mailed on Feb. 21, 2012, 12 pages.
Non Final Office Action received for U.S. Appl. No. 12/501,619, mailed on Nov. 3, 2011, 10 pages.
Non-Final Office Action received for U.S. Appl. No. 12/501,619, mailed on Jan. 28, 2014, 10 pages.
Advisory Action Received for U.S. Appl. No. 12/581,295, mailed on Jul. 3, 2014, 3 pages.
Final Office Action received for U.S. Appl. No, 12/581,295, mailed on Jun. 5, 2014, 14 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Final Office Action received for U.S. Appl. No. 12/611,997, mailed on Dec. 11, 2012, 9 pages.
Final Office Action received for U.S. Appl. No. 12/611,997, mailed on Nov. 10, 2011, 15 pages.
Final Office Action received for U.S. Appl. No. 12/611,997, mailed on Oct. 24, 2013, 10 pages.
Non Final Office Action received for U.S. Appl. No. 12/611,997, mailed on Nov. 26, 2014, 8 pages.
Non Final Office Action received for U.S. Appl. No. 12/611,997, mailed on Apr. 8, 2013, 9 pages.
Non Final Office Action received for U.S. Appl. No. 12/611,997, mailed on Aug. 24, 2012, 11 pages.
Non Final Office Action received for U.S. Appl. No. 12/611,997, mailed on Jun. 21, 2011, 13 pages.
Non-Final Office Action received for U.S. Appl. No. 12/611,997, mailed on Feb. 13, 2014, 9 pages.
Notice of Allowance received for U.S. Appl. No. 12/611,997, mailed on Apr. 15, 2015, 7 pages.
Advisory Action Received for U.S. Appl. No. 13/049,199 mailed on Jun. 7, 2012, 3 pages.
Final Office Action received for U.S. Appl. No. 13/049,199, mailed on Apr. 4, 2012, 10 pages.
Final Office Action received for U.S. Appl. No. 13/049,199 mailed on Aug. 11, 2014, 8 pages.
Non Final Office Action received for U.S. Appl. No. 13/049,199, mailed on Dec. 12, 2011, 10 pages.
Non-Final Office Action received for U.S. Appl. No. 13/049,199, mailed on Feb. 4, 2014, 8 pages.
Notice of Allowance received for U.S. Appl. No. 13/049,199, mailed on Dec. 15, 2014, 7 pages.
Final Office Action received for U.S. Appl. No. 13/207,381, mailed on Nov. 2, 2012, 7 pages.
Final Office Action received for U.S. Appl. No. 13/207,381, mailed on Nov. 7, 2013, 7 pages.
Non Final Office Action received for U.S. Appl. No. 13/207,381, mailed on Nov. 25, 2014, 5 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.

(56) References Cited

OTHER PUBLICATIONS

Non-Final Office Action received for U.S. Appl. No. 13/207,381, mailed on Feb. 25, 2014, 8 pages.
Non Final Office Action received for U.S. Appl. No. 13/232,730, mailed on Apr. 23, 2013, 10 pages.
Advisory Action received for U.S. Appl. No. 13/267,383, mailed on Jan. 6, 2014, 4 pages.
Final Office Action received for U.S. Appl. No. 13/267,383, mailed on Oct. 25, 2013, 8 pages.
Non-Final Office Action received for U.S. Appl. No. 13/267,383, mailed on Feb. 25, 2015, 9 pages.
Non Final Office Action received for U.S. Appl. No. 13/291,875 mailed on Feb. 28, 2013, 8 pages.
Notice of Allowance received for U.S. Appl. No. 13/291,875, mailed on Sep. 17, 2013, 11 pages.
Non Final Office Action received for U.S. Appl. No. 13/465,264, mailed on Oct. 29, 2014, 13 pages.
Non-Final Office Action received for U.S. Appl. No. 13/465,264, mailed on Dec. 23, 2014, 13 pages.
Final Office Action received for U.S. Appl. No. 13/646,570, mailed on Dec. 23, 2014, 10 pages.
Non Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Notice of Allowance received for U.S. Appl. No. 13/831,543, mailed on Oct. 8, 2014, 14 pages.
Notice of Allowance received for U.S. Appl. No. 14/046,635, mailed on Dec. 17, 2013, 7 pages.
Non-Final Office Action received for U.S. Appl. No. 14/061,554, mailed on Mar. 12, 2014, 14 pages.
Notice of Allowance received for U.S. Appl. No. 14/061,554, mailed on Apr. 25, 2014, 8 pages.
Non Final Office Action received for U.S. Appl. No. 14/079,463, mailed on Mar. 4, 2014, 9 pages.
Notice of Allowance received for U.S. Appl. No. 14/079,463, mailed on Apr. 1, 2014, 5 pages.
Non-Final Office Action received for U.S. Appl. No. 14/271,276, mailed on Aug. 4, 2014, 7 pages.
Notice of Allowance received for U.S. Appl. No. 14/271,276, mailed on Feb. 25, 2015, 8 pages.
Final Office Action received for U.S. Appl. No. 14/271,342 mailed on Feb. 27, 2015, 7 pages.
Non-Final Office Action received for U.S. Appl. No. 14/271,342, mailed on Sep. 2, 2014, 6 pages.
Notice of Acceptance Received for Australian Patent Application No. 2009257368, mailed on Aug. 28, 2014, 2 pages.
Office Action received for Australian Patent Application No. 2009257368, issued on Apr. 28, 2014, 4 pages.
Office Action received for Australian Patent Application No. 2009257368, issued on Jul. 31, 2013, 4 pages.
Notice of Acceptance Received for Australian Patent Application No. 2009313507, mailed on Nov. 17, 2014, 2 pages.
Office Action received for Australian Patent Application No. 2009313507, issued on Nov. 13, 2013, 3 pages.
Office Action received for Chinese Patent Application No. 200980153687.X, mailed on Dec. 26, 2012, 11 pages.
Office Action received for Chinese Patent Application No. 200980153687.X, mailed on Jul. 11, 2013, 11 pages.
Decision to Grant received for Japanese Patent Application No. 2011-513694, mailed on Oct. 7, 2014, 3 pages.
Office Action received for Japanese Patent Application No. 2011-513694, mailed on Aug. 27, 2013, 6 pages.
Office Action Received for Japanese Patent Application No. 2011-513694, mailed on Jun. 10, 2014, 2 pages.
Office Action Received for Japanese Patent Application No, 2011-534914, mailed on Jan. 13, 2015, 2 pages.
Office Action Received for Japanese Patent Application No. 2011-534914, mailed on Jul. 15, 2014, 3 pages.
Office Action received for Japanese Patent Application No. 2011-534914, mailed on Oct. 1, 2013, 5 pages.
Adams, John M. , "Unpublished U.S. Appl. No. 14/273,063, filed May 8, 2014, title "Shock Wave Guide Wire"", 24 pages.
Cleveland et al., "The Physics of Shock Wave Lithotripsy", Extracorporeal Shock Wave Lithotripsy Part IV, Chapter 38, 2012, pp. 317-332.
Connors et al, "Renal Nerves Mediate Changes in Contralateral Renal Blood Flow after Extracorporeal Shockwave Lithotripsy", Nephron Physiol, vol. 95, 2003, pp. 67-75.
Gambihler et al., "Permeabilization of the Plasma Membrane of LI210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep vol. 14, 2012, pp. 567-572.
Hawkins et al., U.S. Appl. No. 61/061,170, filed Jun. 13, 2008, titled "Shockwave Balloon Catheter System".
Kodama et al., "Shock Wave-Mediated Molecular Delivery into Cells", Biochimica et Biophysics Acta vol. 542, 2002, pp. 186-194.
Lauer et al., "Shock Wave Permeabilization as a New Gene Transfer Method", Gene Therapy vol. 4, 1997, pp. 710-715.
International Preliminary Report on Patentability received for PCT Patent Application No. PCT/US2009/047070, mailed on Dec. 23, 2010, 7 pages.
International Search Report received for PCT Patent Application No. PCT/US2009/047070, mailed on Jan. 19, 2010, 4 pages.
International Written Opinion received for PCT Patent Application No. PCT/US2009/047070, mailed on Jan. 19, 2010, 5 pages.
International Preliminary Report on Patentability received for PCT Patent Application No. PCT/US2009/063354, mailed on May 19, 2011, 6 pages.
International Search Report received for PCT Patent Application No. PCT/US2009/063354, mailed on Jun. 11, 2010, 3 pages.
International Written Opinion received for PCT Patent Application No. PCT/US2009/063354, mailed on Jun. 11, 2010, 4 pages.
International Preliminary Report on Patentability received for PCT Patent Application No. PCT/US2011/047070, mailed on Feb. 21, 2013, 7 pages.
International Written Opinion received for PCT Patent Application No. PCT/US2011/047070, mailed on May 1, 2012, 5 pages.
International Preliminary Report on Patentability received for PCT Patent Application No. PCT/US2011/051606, issued on May 14, 2013, 6 pages.
International Search Report and Written Opinion received for PCT Patent Application No. PCT/US2011/051606, mailed on Apr. 24, 2012, 9 pages.
International Preliminary Report on Patentability received for PCT Patent Application No. PCT/US2012/023172, mailed on Aug. 15, 2013, 6 pages.
International Search Report received for PCT Patent Application No. PCT/US2012/023172, mailed on Sep. 28, 2012, 3 pages.
International Written Opinion received for PCT Patent Application No. PCT/US2012/023172, mailed on Sep. 28, 2012, 4 pages.
International Preliminary Report on Patentability received for PCT Patent Application No. PCT/US2012/063925, mailed on May 22, 2014, 12 pages.
International Search Report received for PCT Patent Application No. PCT/US2012/063925, mailed on Mar. 25, 2013, 3 pages.
International Written Opinion received for PCT Patent Application No. PCT/US2012/063925, mailed on Mar. 25, 2013, 9 pages.
International Preliminary Report on Patentability received for PCT Patent Application No. PCT/US2013/031805, mailed on Feb. 19, 2015, 11 pages.
International Search Report and Written Opinion received for PCT Patent Application No. PCT/US2013/031805, mailed on May 20, 2013, 13 pages.
International Preliminary Report on Patentability received for PCT Patent Application No. PCT/US2013/039987, issued on Nov. 20, 2014, 11 pages.
International Search Report and Written Opinion received for PCT Patent Application No. PCT/US2013/039987, mailed on Sep. 23, 2013, 15 pages.

(56) References Cited

OTHER PUBLICATIONS

International Preliminary Report on Patentability received for PCT Patent Application No. PCT/US2013/048277, mailed on Jan. 8, 2015, 9 pages.
International Search Report and Written Opinion received for PCT Patent Application No. PCT/US2013/048277, mailed on Oct. 2, 2013, 14 pages.
International Preliminary Report on Patentability received for PCT Patent Application No. PCT/US2013/053292, mailed on Feb. 19, 2015, 9 pages.
International Search Report and Written Opinion received for PCT Patent Application No. PCT/US2013/053292, mailed on Nov. 4, 2013, 14 pages.
International Search Report and Written Opinion received for PCT Patent Application No. PCT/US2013/054104, mailed on Oct. 22, 2013, 12 pages.
International Preliminary Report on Patentability received for PCT Patent Application No. PCT/US2013/055431, mailed on Feb. 26, 2015, 7 pages.
International Search Report and Written Opinion received for PCT Patent Application No. PCT/US2013/055431, mailed on Nov. 12, 2013, 9 pages.
International Preliminary Report on Patentability received for PCT Patent Application No. PCT/US2013/059533 mailed on Mar. 26, 2015, 10 pages.
International Search Report and Written Opinion received for PCT Patent Application No. PCT/US013/059533, mailed on Nov. 7, 2013, 14 pages.
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Notice of Allowance received for U.S. Appl. No. 13/049,199, mailed on Jan. 13, 2015, 4 pages.
Notice of Allowance received for U.S. Appl. No. 13/957,276, mailed on Aug. 28, 2015, 9 pages.
Advisory Action received for U.S. Appl. No. 14/229,735, mailed on Nov. 3, 2015, 3 pages.
Final Office Action received for U.S. Appl. No. 14/229,735, mailed on Aug. 27, 2015, 7 pages.
Notice of Allowance received for Canadian Patent Application No. 2,727,429, mailed on May 26, 2015, 1 page.
Office Action Received for Japanese Patent Application No. 2014-158517, mailed on May 19, 2015, 5 pages (2 pages of English Translation and 3 pages of Official Copy).
Decision to Grant received for European Patent Application No. 09825393.3, mailed on Mar. 13, 2014, 2 pages.
Non-Final Office Action received for U.S. Appl. No. 13/962,315, mailed on Aug. 26, 2015, 20 pages.
Notice of Allowance received for U.S. Appl. No. 14/229,735, mailed on Nov. 17, 2015, 5 pages.
Non Final Office Action received for U.S. Appl. No. 14/515,130, mailed on Jan. 14, 2016, 16 pages.
Office Action received for Canadian Patent Application No. 2,779,600, mailed on Jan. 4, 2016, 6 pages.
International Preliminary Report on Patentability received for PCT Patent Application No. PCT/US2013/054104, mailed on Feb. 19, 2015, 8 pages.
International Search Report and Written Opinion received for PCT Patent Application No. PCT/US2015/060453, mailed on Jan. 21, 2016, 15 pages.

* cited by examiner

SHOCKWAVE VALVULOPLASTY CATHETER SYSTEM

CLAIM OF PRIORITY

The present application is a continuation of U.S. patent application Ser. No. 12/611,997, filed Nov. 4, 2009, which claims the benefit of U.S. Provisional Patent Application Ser. No. 61/111,600, filed Nov. 5, 2008, each of which is incorporated herein by reference in its entirety.

BACKGROUND OF THE INVENTION

Aortic calcification, also called aortic sclerosis, is a buildup of calcium deposits on the aortic valve in the heart. This often results in a heart murmur, which can easily be heard with a stethoscope over the heart. However, aortic calcification usually doesn't significantly affect the function of the aortic valve.

In some cases, though, the calcium deposits thicken and cause narrowing at the opening of the aortic valve. This impairs blood flow through the valve, causing chest pain or a heart attack. Doctors refer to such narrowing as aortic stenosis.

Aortic calcification typically affects older adults. But when it occurs in younger adults, it's often associated with an aortic valve defect that is present at birth (congenital) or with other illnesses such as kidney failure. An ultrasound of the heart (echocardiogram) can determine the severity of aortic calcification and also check for other possible causes of a heart murmur.

At present there is no specific treatment for aortic calcification. General treatment includes the monitoring for further developments of heart disease. Cholesterol levels are also checked to determine the need for medications to lower cholesterol in the hope to prevent progression of aortic calcification. If the valve becomes severely narrowed, aortic valve replacement surgery may be necessary.

The aortic valve area can be opened or enlarged with a balloon catheter (balloon valvuloplasty) which is introduced in much the same way as in cardiac catheterization. With balloon valvuloplasty, the aortic valve area typically increases slightly. Patients with critical aortic stenosis can therefore experience temporary improvement with this procedure. Unfortunately, most of these valves narrow over a six to 18 month period. Therefore, balloon valvuloplasty is useful as a short-term measure to temporarily relieve symptoms in patients who are not candidates for aortic valve replacement. Patients who require urgent noncardiac surgery, such as a hip replacement, may benefit from aortic valvuloplasty prior to surgery. Valvuloplasty improves heart function and the chances of surviving non-cardiac surgery. Aortic valvuloplasty can also be useful as a bridge to aortic valve replacement in the elderly patient with poorly functioning ventricular muscle. Balloon valvuloplasty may temporarily improve ventricular muscle function, and thus improve surgical survival. Those who respond to valvuloplasty with improvement in ventricular function can be expected to benefit even more from aortic valve replacement. Aortic valvuloplasty in these high risk elderly patients has a similar mortality (5%) and serious complication rate (5%) as aortic valve replacement in surgical candidates.

The present invention provides an alternative treatment system for stenotic or calcified aortic valves. As will be seen subsequently, the embodiments described herein provide a more tolerable treatment for aortic stenosis and calcified aortic valves than the currently performed aortic valve replacement. The invention also provides a more effective treatment than current valvuloplasty therapy.

SUMMARY OF THE INVENTION

In one embodiment, a valvuloplasty system comprises a balloon adapted to be placed adjacent leaflets of a valve, the balloon being inflatable with a liquid, and a shock wave generator within the balloon that produces shock waves that propagate through the liquid for impinging upon the valve. The balloon may be adapted to be placed on opposite sides of the valve leaflets or within the valve annulus.

The system may further comprise an elongated tube. The balloon may be at the distal end of the elongated tube.

The balloon may include a first balloon chamber and a second balloon chamber. The first and second balloon chambers may be longitudinally spaced from each other.

The elongated tube may include a lumen. The first and second balloon chambers are in fluid communication with the elongated tube lumen.

The shock wave generator may comprise a first shock wave source within the first balloon chamber and a second shock wave source within the second balloon chamber. The first and second shock wave sources may comprise a first electrical arc generator and a second electrical arc generator. The electrical are generators may comprise at least one electrode adapted for connection to a voltage pulse generator. Each of the electrical arc generators may comprise an electrode pair adapted for connection to a voltage pulse generator. Each of the electrode pairs may comprise a pair of coaxially arranged electrodes.

They may further comprise a high voltage catheter including the first and second electrical arc generators. The first and second electrical arc generators may be longitudinally spaced from each other for being received within the first and second balloon chambers, respectively.

As mentioned above, the balloon may be adapted to be placed within the valve annulus. To that end, the balloon may have a reduced diameter portion adapted to be received within the valve annulus.

The balloon may be formed of a compliant material.

Alternatively, the balloon may be formed of a non-compliant material.

According to another embodiment, a catheter system comprises an elongated carrier and a balloon carried by the elongated carrier. The balloon is arranged to receive a fluid therein that inflates the balloon. The system further includes at least one arc generator including at least one pair of coaxially arranged electrodes within the balloon that forms a mechanical shock wave within the balloon.

The system may further include a cable comprising a center conductor and an outer conductive shield insulated from the inner conductor. A first one of the coaxially arranged electrodes may be at least in part formed by the center conductor of the cable, and a second one of the coaxially arranged electrodes may be at least in part formed by the outer conductive shield of the cable.

According to a further embodiment, a valvuloplasty method for treating a valve having leaflets and an annulus comprises placing a balloon adjacent to the leaflets of the valve, inflating the balloon with a liquid, and producing shock waves within the balloon that propagate through the liquid for impinging upon the valve leaflets and the valve annulus.

The placing steps may be performed by placing the balloon on opposite sides of the valve leaflets. Alternatively the placing step may be performed by placing the balloon within the valve annulus.

BRIEF DESCRIPTION OF THE DRAWINGS

The features of the present invention which are believed to be novel are set forth with particularity in the appended claims. The various described embodiments of the invention, together with representative features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
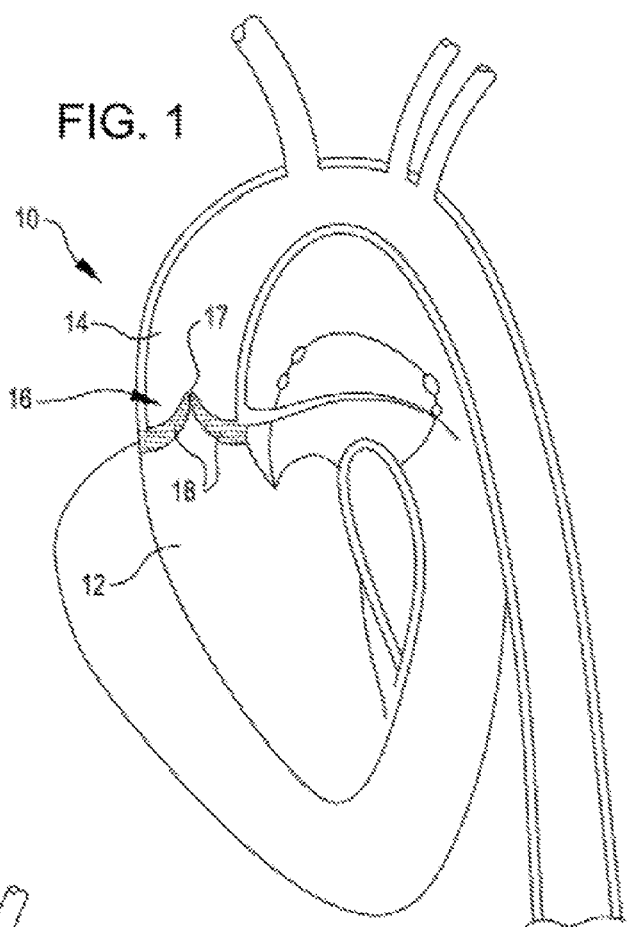
FIG. 1 is a cut away view of the left ventricle, the aorta, and the aortic valve of a heart showing a reduced aortic valve open area and thickened valve leaflets due to calcium and fibrotic tissue.

Referring now to FIG. 1, it is a cut away view of the left ventricle 12, the aorta 14, and the aortic valve 16 of a heart 10 with a stenotic and calcified aortic valve 16. Here more particularly, it may be seen that the opening 17 of the stenotic and calcified aortic valve 16 is restricted in size and that the valve leaflets 18 are thickened with calcium deposits and fibrotic tissue. The thickened leaflets 18 and smaller valve opening 17 restrict blood flow from the heart creating excess work for the heart 10 and poor cardiac output. As previously mentioned, current treatment includes replacement of the valve or attempts too stretch the valve annulus with a balloon.

Figure 2:
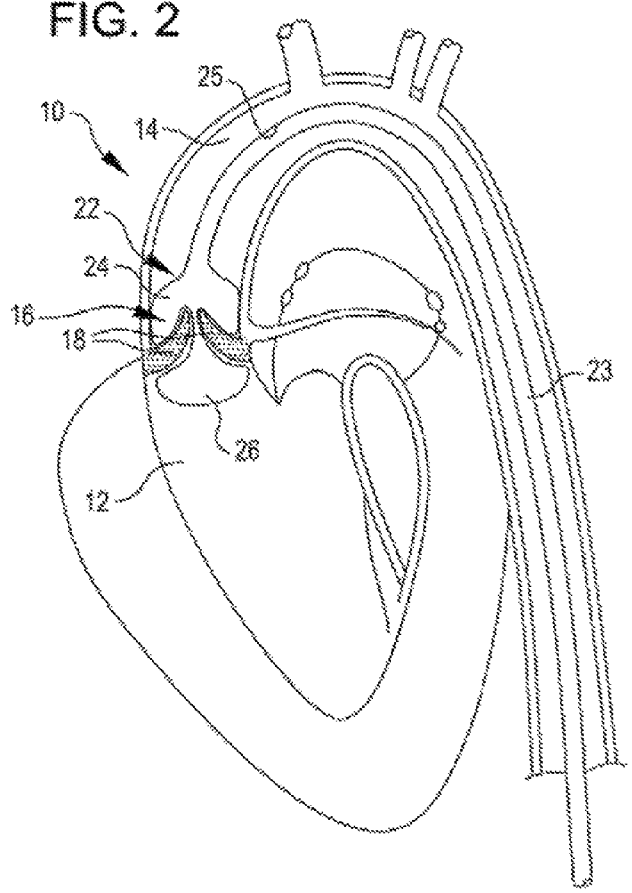
FIG. 2 is a cut away view of the aortic valve of a heart with a treatment balloon placed on both sides of the aortic valve leaflets, according to an embodiment of the present invention.

FIG. 2 is a cut away view of the aortic valve 16 with a treatment balloon 22 placed on both sides of the aortic valve leaflets 18. The balloon 22 may be formed from a compliant or a non-compliant material. The balloon, as seen in FIG. 2, is at the distal end of an elongated tube 23. The treatment balloon 22 has two longitudinally spaced chambers 24 and 26 that share a common inflation lumen 25 of the tube 23. Alternatively the balloon chambers 24 and 26 may not share the same inflation fluid path. The chambers 24 and 26 are longitudinally spaced such that chamber 24 is positioned on one side of the aortic valve leaflets 18 and chamber 26 is positioned on the other side of the aortic valve leaflets 18. The chambers 24 and 26 are inflated with saline/contrast mixture, for example. Each chamber 24 and 26 may contain an electrode (as shall be seen subsequently) that can produce electrical arcs to deliver timed shock waves. The shock waves can be synchronized to concurrently impinge upon both sides of the leaflets 18 to maximize the effectiveness of breaking calcium deposits. Such shock waves may be generated and also synchronized to the R wave of the heart 10 in a manner as described for example in co-pending application No. 61/061,170 filed on Jun. 13, 2008, which application is incorporated herein in its entirety.

Figure 3:
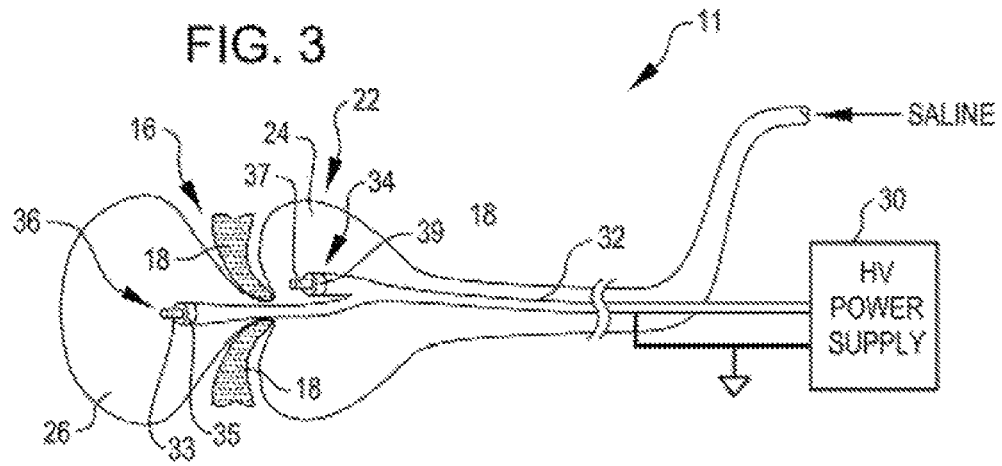
FIG. 3 is a schematic view of a dual shockwave balloon embodying the invention attached to a high voltage power supply.

FIG. 3 is a schematic view of a valvuloplasty system 11 embodying the present invention. The system 11 includes the dual shockwave balloon 22. The balloon 22 has received a high voltage catheter 32 that is connected to a high voltage power supply 30. The schematic representation shows the positioning of the balloon chambers 24 and 26 above and below the leaflets 18 of the aortic valve 16. As previously described, shock waves will impinge upon opposite sides of the leaflets 18 to more effectively break calcium deposits in the valve leaflets 18. The annulus will also be treated in this arrangement. To that end, the high voltage catheter 32 includes electrode pairs 34 and 36 that are coaxially arranged electrodes placed in chambers 24 and 26 respectively of the balloon 22. More specifically, electrode pair 34 is at the distal end of a first cable and comprises a center conductor 33 and an outer conductive shield 35. Similarly, electrode pair 34 is at the distal end of a second cable and comprises a center conductor 37 and an outer conductive shield 39. High voltage pulses from power supply 30 are applied to the electrode pairs 34 and 36 in a manner as described in the aforementioned application Ser. No. 61/061,170 to create shockwaves within the fluid within the chambers 24 and 26 of the balloon 22. The shock waves impinge upon the valve leaflets 18 and the valve annulus to cause the break up of calcium deposits and fibrotic tissue on the valve leaflets 18 and annulus to open the aortic valve 16.

Figure 4:
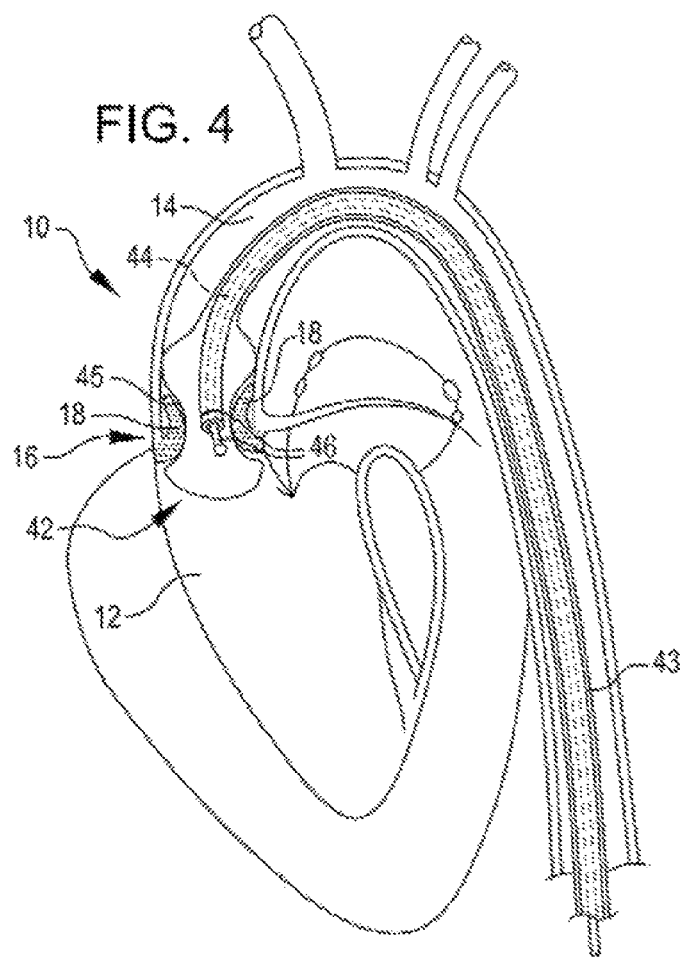
FIG. 4 is a cut away view of a heart showing an alternate valvuloplasty shock wave balloon according to a further embodiment and aspects of the present invention.

FIG. 4 shows an alternate valvuloplasty shock wave balloon 42 at the distal end of an elongated tube 43. The balloon 42 is placed in the annulus of the aortic valve 16. To that end, the balloon 42 has a reduced diameter portion 45 for being received within the valve annulus. The balloon 42 has a high voltage catheter 44 therein that terminates in an electrode pair 46. As in the previous embodiment, the electrode pair 46 may comprise a pair of coaxially arranged electrodes where a center conductor may form at least a part of one electrode and at an outer conductive shield may form at least a part of the other electrode. The catheter 44 and its electrode pair 46 provide shock waves as previously described. Such an arrangement will decalcify the leaflets 18. This not only will decalcify the leaflets 18, but will also soften the aortic valve annulus and expand its diameter. Hence, the balloon 42 provides the added advantage of exerting expansion pressure directly to the annulus of the valve to remodel the annulus diameter.

While particular embodiments of the present invention have been shown and described, modifications may be made, and it is therefore intended to cover all such changes and modifications which fall within the true spirit and scope of the invention.

What is claimed is:

1. An intravascular valvuloplasty system for breaking calcium deposits on the leaflets of an aortic valve, each leaflet connected to a wall and having a concave region, comprising:
   an elongate body;
   a balloon being inflatable with a liquid via an inflation lumen provided in the elongate body, wherein the inflated balloon has a portion shaped to fit within the concave region of a leaflet and between the leaflet and the wall; and
   a shock wave generator for generating shock waves that propagate through the liquid for impinging upon the leaflets and breaking calcium deposits on the leaflets.

2. The system of claim 1, wherein the balloon is at the distal end of the elongate body.

3. The system of claim 1 wherein the shock wave generator includes an electric arc generator.

4. The system of claim 3 wherein the electric arc generator includes at least one pair of electrodes and a power supply connected to the electrodes for generating high voltage pluses between the electrodes.

5. The system of claim 4 wherein the pair of electrodes comprises an inner electrode and an outer electrode shield that surrounds the inner electrode.

6. An intravascular valvuloplasty method for breaking calcium deposits on the leaflets of an aortic valve, each leaflet connected to the wall of the aorta and having a concave region, comprising:

advancing an elongated tube into the region of the aortic valve, said tube including a fluid lumen, said elongated tube including a balloon on the distal end thereof, said balloon carrying a shock wave generator located between the tube and the inner surface of the balloon;

inflating the balloon with a liquid delivered through the fluid lumen in a manner so that a portion of the balloon fits within the concave region of a leaflet between the leaflet and the wall; and energizing the shock wave generator to produce a shock wave within the balloon that propagates through the liquid for impinging upon the valve leaflet in order to break calcium deposits on the leaflet.

7. The method of claim 6 wherein the shock wave generator includes an electric arc generator and the step of energizing the shock wave generator is performed by delivering high voltage pulses from a power supply to the electric arc generator.

8. The method of claim 7 wherein the electric arc generator includes at least one pair of electrodes.

9. The method of claim 8 wherein the pair of electrodes comprises an inner electrode and an outer electrode shield that surrounds the inner electrode.

10. An intravascular valvuloplasty method for breaking calcium deposits on an aortic valve having leaflets, comprising:

advancing an elongated tube into the region of the aortic valve, said tube including at least one fluid lumen, said elongated tube carrying two balloon chambers near the distal end thereof;

inflating the balloon chambers with a liquid delivered through the at least one fluid lumen, with one balloon chamber being positioned on one side of the valve and the other balloon chamber being positioned on the other side of the valve, each of said balloon chambers having a shock wave generator located therein; and energizing both of the shock wave generators in both balloon chambers so that the shock waves generated thereby impinge on both sides of the leaflets in order to break calcium deposits on the leaflets.

11. A method as recited in claim 10 wherein the shock wave generators in both balloon chambers are synchronized so that the shock waves generated thereby impinge concurrently on both sides of the leaflets.

12. A method as recited in claim 11 wherein both balloon chambers are inflated via a common fluid lumen.

13. A method as recited in claim 11 wherein the balloon chambers are inflated with separate fluid lumens.

14. The method of claim 11 wherein each shock wave generator includes an electric arc generator and the step of energizing the shock wave generators is performed by delivering high voltage pulses to the electric arc generators.

15. The method of claim 14 wherein each electric arc generator includes at least one pair of electrodes.

16. The method of claim 15 wherein the pair of electrodes comprises an inner electrode and an outer electrode shield that surrounds the inner electrode.

* * * * *